(12) United States Patent
de Rigal et al.

(10) Patent No.: US 6,724,480 B2
(45) Date of Patent: Apr. 20, 2004

(54) COMPARISON SAMPLE FOR SIMULATING AN APPEARANCE OF A KERATINOUS ELEMENT, AND RELATED METHODS

(75) Inventors: Jean de Rigal, Claye Souilly (FR); Christophe Dauga, Levallois-Perret (FR)

(73) Assignee: L'Oreal S.A., Paris (FR)

( * ) Notice: Subject to any disclaimer, the term of this patent is extended or adjusted under 35 U.S.C. 154(b) by 68 days.

(21) Appl. No.: 10/006,890

(22) Filed: Dec. 10, 2001

(65) Prior Publication Data

US 2002/0140936 A1 Oct. 3, 2002

(30) Foreign Application Priority Data

Dec. 8, 2000 (FR) .............................. 00 16001

(51) Int. Cl.$^7$ ................................. G01J 3/52
(52) U.S. Cl. ................. 356/422; 356/421; 356/394; 434/99; 600/300
(58) Field of Search .................. 356/421–422, 356/392, 394; 434/98–100; 600/300

(56) References Cited

U.S. PATENT DOCUMENTS

| | | | |
|---|---|---|---|
| 1,741,080 A | | 12/1929 | Stenz |
| 5,150,791 A | * | 9/1992 | Kamen et al. .............. 434/100 |
| 5,311,293 A | | 5/1994 | MacFarlane et al. |
| 5,643,341 A | * | 7/1997 | Hirsch et al. .............. 434/100 |
| 5,852,675 A | | 12/1998 | Matsuo et al. |
| 6,157,445 A | | 12/2000 | Macfarlane et al. |
| 2002/0065456 A1 | * | 5/2002 | Bazin et al. ................. 600/407 |

FOREIGN PATENT DOCUMENTS

FR          2 540 991          8/1984

OTHER PUBLICATIONS

Co–pending Application—Attorney Docket No. 08048.0021–00000 Title: A Comparison Sample for Simulating the Color of Keratinous Elements, and Related Methods Inventor(s): Jean DE RIGAL et al. U.S.filing Date: Dec. 10, 2001.
Patent Abstracts of Japan, vol. 017, No. 457, Aug. 20, 1993 (JP 05 107115 A).
Patent Abstracts of Japan, vol. 1997, No. 09, Sep. 30, 1997, (JP 09 133584 A).
English language Derwent Abstract of FR 2 540 991, Aug. 17, 1984.

* cited by examiner

*Primary Examiner*—F. L. Evans
*Assistant Examiner*—Kara Geisel
(74) *Attorney, Agent, or Firm*—Finnegan, Henderson, Farabow, Garrett & Dunner, LLP (57) ABSTRACT

A system comprising a plurality of comparison samples configured to substantially simulate the appearance of a keratinous element. Each comparison sample may be configured to substantially simulate both a color and an appearance characteristic other than color of the keratinous element.

157 Claims, 5 Drawing Sheets

FIG_1

FIG_4

FIG_5

FIG_6

FIG_7

FIG_8

FIG_9

FIG_12

FIG_10

FIG.11

COMPARISON SAMPLE FOR SIMULATING AN APPEARANCE OF A KERATINOUS ELEMENT, AND RELATED METHODS

The present invention relates to a comparison sample for simulating the appearance of a keratinous element such as the skin, including the lips, the fingernails, the toenails, or the hair, for example.

There exists a need for reliably simulating the appearance of the skin, including the lips, the fingernails, the toenails, the hair, or other keratinous elements. It should be understood that the invention could be practiced without performing one or more of the aspects described. Other aspects will become apparent from the detailed description that follows.

As embodied and broadly described herein, an aspect of the invention may include at least one comparison sample configured to substantially simulate an appearance of a keratinous element, such as the skin, wherein the comparison sample substantially simulates both a color and an appearance characteristic other than color of the keratinous element.

In one example, at least two comparison samples may substantially simulate an appearance characteristic other than color to differing degrees.

The comparison samples according to exemplary embodiments thus may substantially simulate not only differing colors but also at least one appearance characteristic other than color to differing degrees, thus providing finer distinctions to be made between various types of a keratinous element, in which distinctions may involve considerations other than color. For example, the appearance characteristic other than color may include brightness, shine, relief, or other similar appearance characteristics other than color.

As an example, a system may include at least two comparison samples having differing brightnesses. This may make it possible, for example, to distinguish between a relatively dull or mat skin and a relatively shiny skin, even if the skins have substantially the same color.

A plurality of comparison samples may comprise at least three degrees, (e.g., three, four or five degrees) of the appearance characteristic other than color.

The appearance characteristic other than color may not be restricted to brightness, and may include, for example, color non-uniformity. Thus, at least two comparison samples may have, for example, colors that are distributed differently within each of the comparison samples.

At least two comparison samples may have marks having a color that differs from a background color on which the marks appear. The number of marks and/or their distribution and/or their size, for example, may vary from one sample to another. Such marks may be representative of marks which appear on skin, such as freckles, age marks, or sunspots for example, which may appear as the skin ages or which may appear due to exposure to the sun.

The appearance characteristic other than color may also be nonuniformity of relief. At least two comparison samples may have differing distributions of relief.

The comparison samples may also include nonuniform brightness. Such nonuniformity may be especially suitable when imitating the appearance of skin, or when providing an appearance having a relatively more or less shiny character from one region to the next. Optionally, in order to obtain such nonuniform brightness, the comparison samples may have adjacent individual regions on their surface including differing brightnesses.

The relatively shiny areas may include the presence of a gloss varnish, and the relatively less shiny (or dull) regions may include the presence of a mat varnish. For example, the width of the relatively shiny regions may be about 300 micrometers ($\mu$m) and the width of the relatively dull regions may be about 100 $\mu$m. Such dimensions may be especially suitable when the comparison samples are intended to imitate the appearance of skin.

Optionally, the comparison samples may have a predetermined relief resulting in a non-uniform brightness. The relief may define recesses and plateaus. The plateaus may be covered in gloss varnish while the recesses may not be coated with gloss varnish. However, in another aspect, each comparison sample may have a substantially uniform brightness.

Each comparison sample may be formed using pigments and/or dyes, for example, selected in such a manner that the comparison sample has a reflectance spectrum that is substantially similar to the reflectance spectrum of a keratinous element whose color the comparison sample substantially simulates such that the keratinous element and the comparison sample appear to have substantially the same color under at least two different illuminants. Thus, a user of the comparison samples, such as a beautician, a clinician, or a dermatologist, or a person without any particular qualification in cosmetics or care products, may select a comparison sample under a given illuminant that substantially simulates the color of the keratinous element which is to be evaluated, for example, such that the result of the selection will remain substantially valid under another illuminant. For example, each comparison sample may substantially simulate the color of the keratinous element under at least two of the illuminants, such as D65 (daylight), D50, and A (an incandescent lamp). According to another aspect, the color difference due to a change of illuminant may be less than 4, or for example, less than 2. This may facilitate evaluating the color of skin or the color of another keratinous element without using a lamp having a specific emission spectrum.

In another aspect, the reflectance spectrum of each comparison sample may not vary substantially from the reflectance spectrum of the corresponding keratinous element in a spectral range extending from about 400 nanometers (nm) to about 800 nm.

Optionally, the expression $$1/N(\lambda)\sum_{\lambda} |I_R^{MOD}(\lambda) - I_R^{REF}(\lambda)|/I_R^{REF}(\lambda)$$

where $I_R^{MOD}(\lambda)$ is the intensity of light reflected at wavelength $\lambda$ for the comparison sample, and $I_R^{REF}(\lambda)$ is the intensity of light reflected at the wavelength $\lambda$ for the keratinous element, is less than or equal to about 0.1, for example less than or equal to about 0.05, or even less than or equal to about 0.01.

The comparison samples also may present differing hues, with hue angles ranging from about 40° to about 70°, and/or from about range 46° to about 64° in the CIEL*C*h 1976 color space. There may be at least ten categories of the plurality comparison samples, with each category presenting a hue differing from the hues of the other categories.

The comparison samples also may present differing lightnesses, with lightness levels (L* in the CIEL*C*h 1976 color space) ranging from about 34 to about 75, for example.

The plurality of comparison samples may comprise at least five categories of comparison samples. Each category may, for example, present a particular lightness level differing from that of the other categories.

In another exemplary embodiment, the plurality of comparison samples may include fifty colors substantially corresponding to combinations of ten hues with five lightness levels, for example.

The overall color difference $\Delta E^*C^*h.94$, as measured in the $CIEL^*C^*h$ 1976 color space, between two comparison samples substantially corresponding to adjacent skin colors may remain substantially constant, with the difference ranging from about 1 to about 40, for example, from about 1 to about 20, or about 4, for example.

Within a given comparison sample, color may be substantially uniform and constant over substantially the entire surface of the comparison sample. Alternatively, the color may be substantially nonuniform, so as to imitate the texture of the keratinous element, for example. A comparison sample may receive two color coatings of different colors, which together may be perceived as a mean color.

A comparison sample also may receive a color coating on a support that is not smooth. For example, the sample support having relief, which may be selected so as to imitate the grain of skin, for example.

According to an aspect, a matching chart may comprise at least one comparison sample configured to simulate the appearance of a keratinous element. The at least one comparison sample may be configured to simulate a color and at least one appearance characteristic other than color of the keratinous element.

According to another aspect, a system may comprise a plurality of comparison samples. Each comparison sample may be configured to simulate an appearance of a keratinous element. Further, each comparison sample may be configured to simulate a color and at least one appearance characteristic other than color of the keratinous element.

The at least one appearance characteristic other than color may include brightness. At least two comparison samples may be configured to have differing brightnesses.

According to an aspect, the comparison sample may include a support having a substantially rectangular shape. The support may have a width of approximately 60 millimeters and a length of approximately 100 millimeters.

The color and the at least one appearance characteristic other than color may be provided on at least a surface portion of the support. Each comparison sample may define a hole configured to permit observation of the keratinous element through the hole. The hole may be located at about one third of the length of the comparison sample.

The hole may have a dimension of approximately 20 millimeters. As an example, the hole may be circular and the dimension may be a diameter.

Each comparison sample may comprise an identifier associated with the color and the at least one appearance characteristic other than color of the sample. As an option, the identifier may be an alphanumeric code.

The comparison samples may be configured to simulate the appearance of a keratinous element chosen from hair, skin, a fingernail, and a toenail.

In yet another aspect, each of the comparison samples may be configured to be displayed respectively on a package of a product intended for application to a keratinous element.

The comparison samples may be configured to be displayed via an electronic image.

In another aspect, the system may further include at least one set of comparison samples, wherein the at least one set includes at least some of the plurality of comparison samples having at least one of substantially the same color and substantially the same at least one appearance characteristic other than color.

According to yet another aspect, a method of manufacturing a product intended for application to a keratinous element may be provided. The method may include providing a system of comparison sample and selecting at least one of the plurality of comparison samples. The method may further comprise making a product intended for application to a keratinous element according to the color and the appearance characteristic other than color of the at least one selected comparison sample.

The selecting of the at least one comparison sample may include determining which of the plurality of comparison samples substantially corresponds to a color and an appearance characteristic other than color of the keratinous element to which the product is intended to be applied.

Alternatively, the selecting of further may include determining which of the comparison samples substantially corresponds to a color and an appearance characteristic other than color desired by a user of the product.

The product may be chosen from at least one of a cosmetic product and a care product.

As an example, the product may be chosen from a foundation makeup product, a concealer product, a lip makeup product, a hair coloring product, a hair care product, a nail varnish, a blush, an eyeshadow, a skin coloring product, including self-tanning lotion, for example, and a skin care product, such as, a sun protection product, for example.

In another aspect, the invention includes a method of monitoring treatment of a keratinous element with a product. The method may include providing a system of comparison samples and selecting a comparison sample that substantially corresponds to a color and at least one appearance characteristic other than color of the keratinous element. The method also may include applying a product to the keratinous element and determining whether at least one of the color and the at least one appearance characteristic other than color of the keratinous element to which the product has been applied has changed after applying the product by comparing the keratinous element with the comparison samples of the system.

The providing of the system may include providing the plurality of comparison samples as a set.

The determining which comparison sample substantially corresponds to the color and the at least one appearance characteristic other than color of the keratinous element may include placing the keratinous element adjacent to at least a portion of the comparison sample so as to permit comparison of the keratinous element with the comparison sample.

Each comparison sample may include an identifier associated with at least one of the color and the at least one appearance characteristic other than color of the sample, and the making of the product may further include making the product based on the identifier of the selected comparison sample.

The product may affect the brightness of the keratinous element.

According to yet another aspect, the method may further comprise selecting from a plurality of differing products the product to be applied to the keratinous element, wherein the selecting of the product is based upon the selected comparison sample.

Each of the comparison samples may include an identifier associated with the color and the at least one appearance characteristic other than color of the sample, and wherein each of the plurality of differing products includes an identifier matching one of the identifiers of the comparison samples, and wherein the selecting of the product includes selecting the product comprising the identifier that matches the identifier of the selected comparison sample.

The product may affect the relief of the keratinous element. Alternatively, or additionally, the product may affect the color of the keratinous element.

According to an additional aspect, a method of selecting a product for application to a keratinous element is provided. The method may include providing a system comprising a plurality of comparison samples and selecting a comparison sample of the system having a color and at least one appearance characteristic other than color that substantially corresponds to the keratinous element to which product is to be applied. The method may further comprise selecting a product from a plurality of differing products for application to the keratinous element based on the selected comparison sample.

The method may further include providing each of the plurality of comparison samples on a respective package associated with each of the plurality of differing products.

In another aspect, a method of treating a keratinous element is provided. The method may include providing a system of comparison samples and selecting a comparison sample from the system that corresponds to a desired color and at least one appearance characteristic other than color for the keratinous element, and treating the keratinous element based on the selected comparison sample.

According to another aspect the invention may include, a method of enabling an analysis of a keratinous element comprising transmitting at least one image simulating an appearance of a keratinous element, wherein the image is configured to simulate a color and at least one appearance characteristic other than color of the keratinous element.

The transmitting of the image may include transmitting the image via a network.

According to yet another optional aspect of the invention, the method may further include receiving information relating to a comparison between at least one keratinous element and the at least one image.

Transmitting an image may involve transmission of the image through one or more networks, and/or storage media. Networks may include public works such as the Internet, telephony networks, courier networks (e.g. postal service, United Parcel Service, Federal Express, etc.), private networks, virtual private networks, local area networks, metropolitan area networks, area wide networks, ad hoc networks, or any other mechanism for permitting communication between remote sites, regardless of whether the connection is wired or wireless. In a broader sense, an image may be transmitted physically such as in hard copy form, via mail delivery or other courier delivery. Storage media may include magnetic storage devices, such as floppy disks and hard drives; optical storage devices, such as compact discs; organic storage devices; random access memory; printed media; or any other medium for storing information.

As used herein, the term "providing" is used broadly, and refers to, but is not limited to, making available for use, giving, supplying, obtaining, getting a hold of, acquiring, purchasing, selling, distributing, possessing, making ready for use, manufacturing, assembling, and/or placing in a position ready for use.

Aside from the structural and procedural arrangements set forth above, the invention could include a number of other arrangements, such as those explained hereinafter. It is to be understood, that both the foregoing description and the following description are exemplary.

The accompanying drawings are incorporated in and constitute a part of this specification. The drawings illustrate exemplary embodiments of the invention and, together with the description, serve to explain certain principles. In the drawings.

Reference will now be made in detail to exemplary embodiments of the invention, examples of which are illustrated in the accompanying drawings. Whenever possible, the same reference numbers are used in the drawings and description to refer to the same or like parts.

Figure 1:
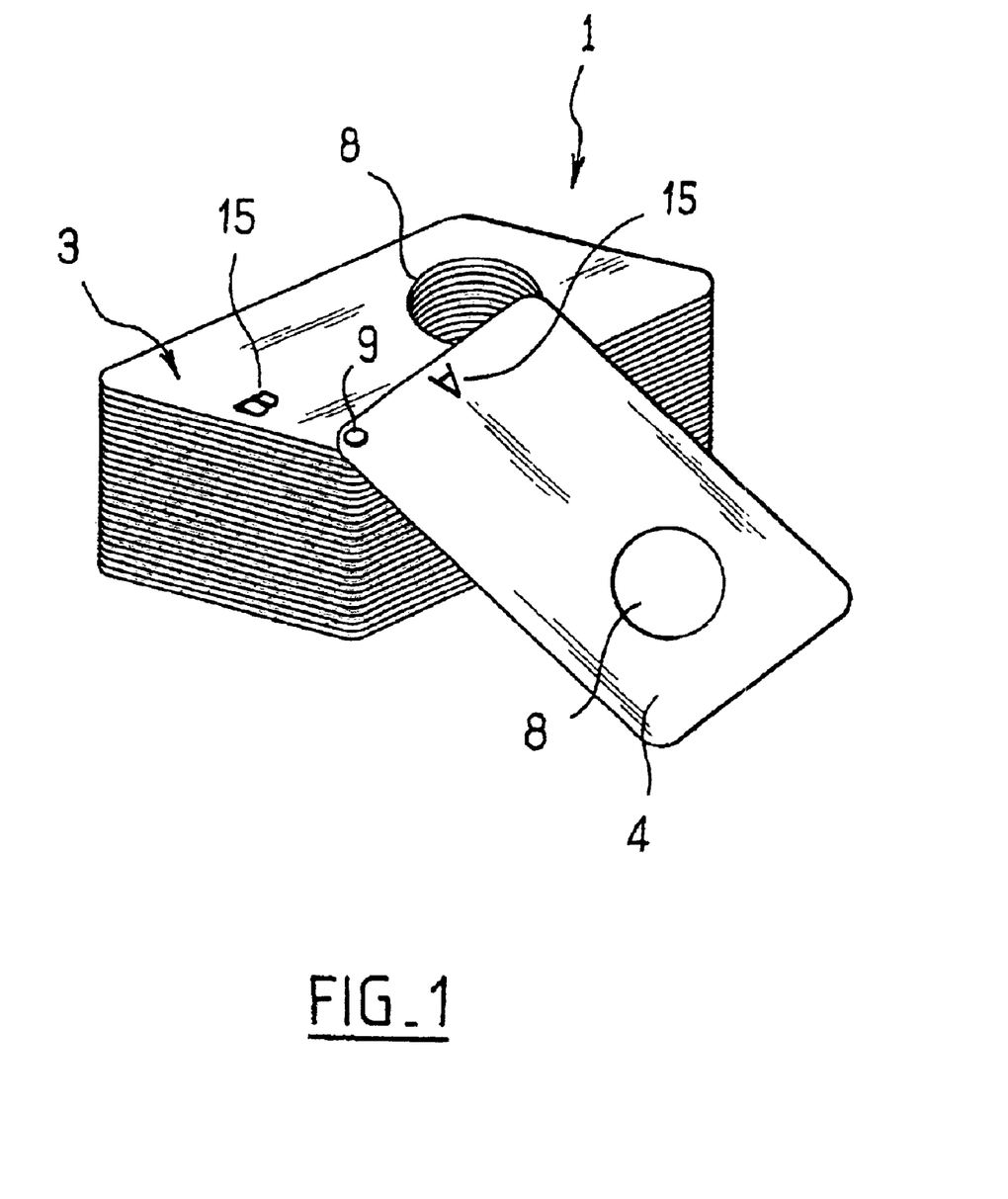
FIG. 1 is a perspective view of an exemplary embodiment of a system of comparison samples.

FIG. 1 shows a system 1, which may be in the form of a matching chart, comprising a plurality of comparison samples 4 each substantially simulating a skin color.

Each comparison sample 4 in the example described comprises a support covered in a colored coating.

Further, each comparison sample comprises a support that is substantially rectangular in shape having dimensions close to 60 mm by 100 mm in the example described. Although the comparison sample in the example shown is rectangular, one having skill in the art would understand that the comparison sample 4 could have other configurations such as, but not limited to, elliptical, oblong, oval, triangular, rectangular, square, and polygonal, or combinations thereof.

Each comparison sample 4 may include a hole 8 passing therethrough in which the hole 8 may be circular and have a diameter of about 20 mm. The hole 8 may be located about one-third of the way along the length of the comparison sample 4. Although the hole 8 in the example shown is circular, one having skill in the art would understand that the hole 8 could have other configurations such as, but not limited to, elliptical, oblong, oval, triangular, rectangular, square, and polygonal, or combinations thereof.

Figure 4:
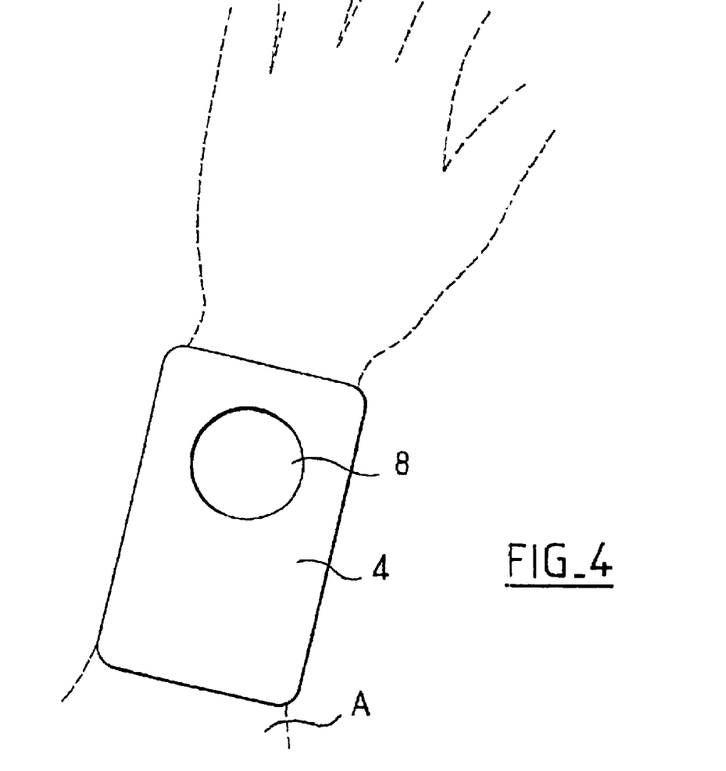
FIG. 4 is a view of an exemplary embodiment of a comparison sample in use for comparison to a person's skin.

The comparison sample 4 may be placed on a portion of the body or the face, including the lips, to compare the color of the sample to the color of the skin. As an example, in FIG. 4, the sample is placed on the forearm A. The hole 8 permits an observer to observe simultaneously the appearance of the skin and the appearance of the comparison sample 4. This may facilitate comparison.

Compared with a square or a circular shape, a comparison sample 4 having a rectangular shape may permit the sample 4 to be oriented in a particular direction when it is in use. This may be preferable when the comparison sample imitates the texture of the skin, since skin texture is anisotropic.

Each comparison sample 4 may include an identifier 15 constituted by one or more alphanumeric characters, for example.

In the example described, the system 1 includes one hundred of comparison samples 4 substantially corresponding to fifty different skin colors and to two different brightnesses per color so as to distinguish between mat skin and shiny skin, for example. In this example, all of the comparison samples 4 have the same texture. The fifty colors may be the result of combining five hues with ten levels of lightness. The hue angles (h) measured in the CIEL*C*h 1976 color space may range from about 40° to about 70°, and/or from about 46° to about 64°. Other combinations and groupings of the comparison samples also are envisioned and considered within the scope of the invention.

In the example described, the lightness levels L* in the CIEL*C*h 1976 color space may range from about 25 to about 80, and/or from about 30 to about 70.

The chroma levels may lie in the range from about 12 to about 30, and/or may be about 22.

The comparison samples 4 can be connected together in a fan-like configuration by being hinged about a pin 9, as shown in FIG. 1. Alternatively, they may be connected together so as to form a set by means of loops 15, as shown in FIGS. 2 and 3, for example.

The comparison samples 4 of the system can be grouped together in various ways. For example, all of the comparison samples 4 can be connected together in a single set 3, as shown in FIG. 1. It also is possible to make up a plurality of sets so as to make the comparison samples 4 easier to handle.

Figure 2:
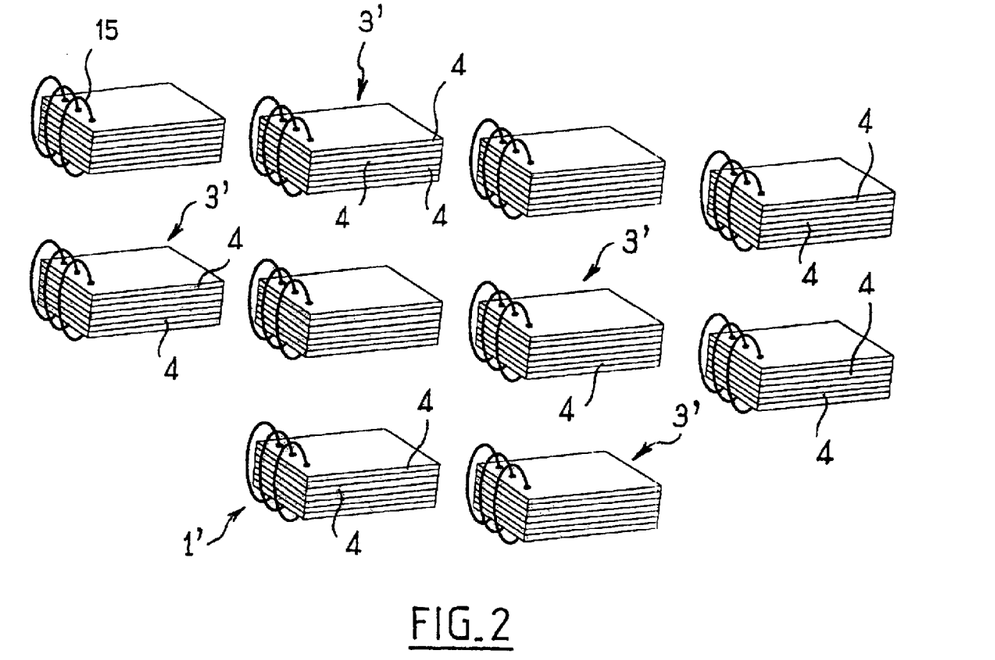
FIG. 2 is a perspective view of another exemplary embodiment of a system of comparison samples in the form of sets of samples.
Figure 3:
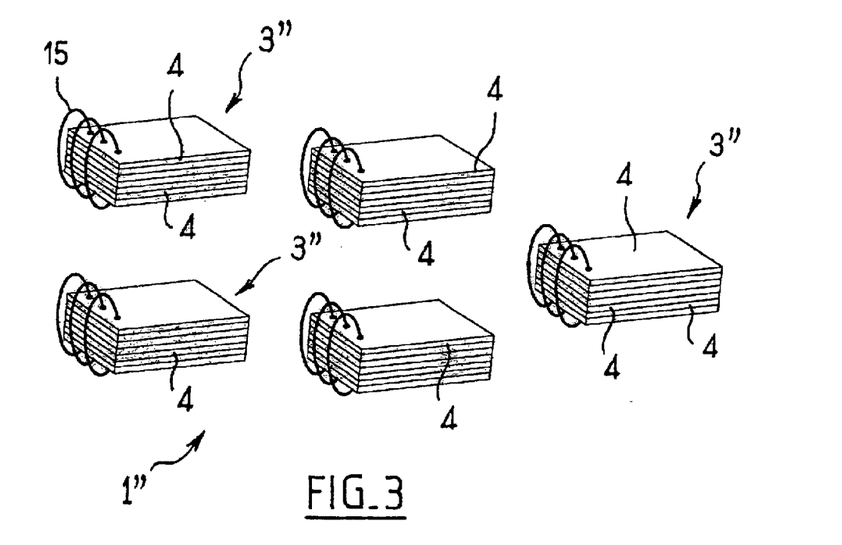
FIG. 3 is a perspective view of yet another exemplary embodiment of a system of comparison samples in the form of sets of samples.

The exemplary embodiment of the system 1' shown in FIG. 2, for example, includes ten sets 3' that may each correspond to a predetermined hue differing from the hues of the other sets. Each set 3' also may be divided further into two subsets comprising five comparison samples 4, for example. Within each subset, the comparison samples 4 may include differing lightness levels while maintaining substantially the same hue.

The brightness of the comparison samples 4 in one set may differ from the brightness of the comparison samples 4 in another set.

The exemplary embodiment of the system 1" shown in FIG. 3 may include five sets 3" of comparison samples 4, with each set 3" substantially corresponding to a predetermined level of lightness differing from the lightness levels of the other sets. Each set 3" may include twenty comparison samples 4 of differing hues, but with each set 3" having substantially the same lightness.

As another example, a given set 3" may have comparison samples 4 having substantially the same hue, but with each set 3" having differing brightnesses.

Of course, the groupings in FIGS. 2–3 are exemplary and other groupings also may be implemented without going beyond the ambit of the present invention.

Figure 11:
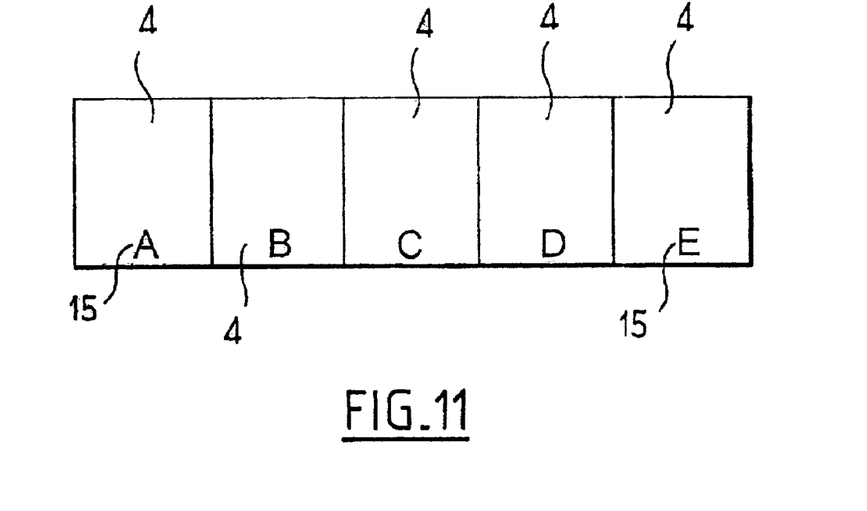
FIG. 11 is a plan view of an exemplary embodiment of a plurality of comparison samples on a support.

By way of example, FIG. 11 shows five comparison samples provided on a common support in the form of a strip. These five comparison samples may all have substantially the same hue, for example, and may have differing lightnesses. Alternatively, they may all have substantially the same lightness, but have with differing hues.

The visual color difference as measured in the CIEL*C*h 1976 color space between two adjacent color comparison samples 4 may be substantially constant, for example, equal to about four. The value may permit an untrained person easily to perceive a variation of color between two comparison samples 4.

The comparison samples 4 may enable skin color to be substantially simulated regardless of the illuminant. For example, the comparison sample 4 may substantially simulate the skin color regardless of whether the illuminant is provided by daylight or artificial lighting of the incandescent or the fluorescent type, for example.

In general, it may be desirable to provide a reflectance spectrum of the comparison sample that corresponds as closely as possible to that of the corresponding skin in the wavelength range 400 nm to 800 nm.

The comparison samples 4 may thus be made on the basis of knowledge concerning the reflectance spectra of all varieties of skin color, including, for example, Caucasian skin, Black skin, or Asiatic skin.

Figure 5:
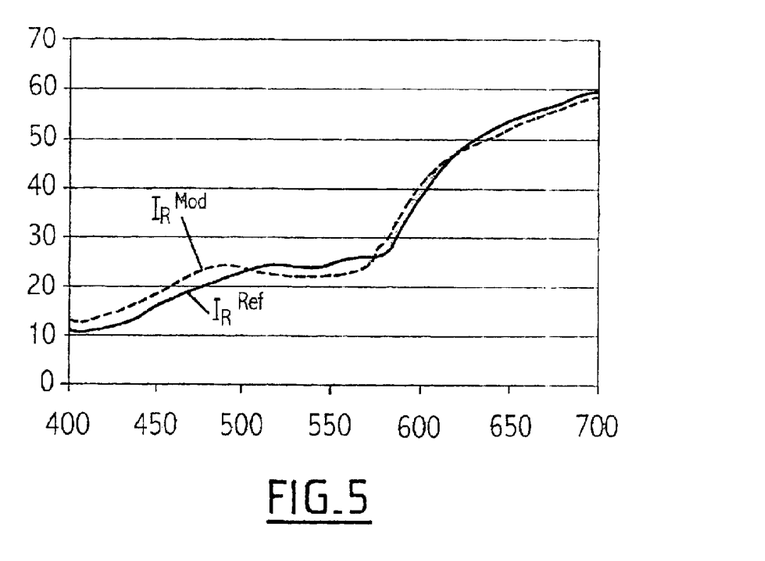
FIG. 5 is an exemplary graph showing the reflectance spectrum of a particular keratinous element and a reflectance spectrum of an exemplary embodiment of a comparison sample that substantially simulates the appearance of the skin.

By way of example, the continuous line in FIG. 5 shows the reflected relative intensity $I_R^{REF}$ (in %) as a function of wavelength (in nm) for a given skin type. The dashed line shows the reflective relative intensity $I_R^{MOD}$ (in %) as a function of wavelength (in nm) for a corresponding comparison sample.

Optionally, $\Delta$, i.e. the quantity $$1/N(\lambda) \sum_\lambda |I_R^{MOD}(\lambda) - I_R^{REF}(\lambda)| / I_R^{REF}$$

may be less than or equal to about 0.01, for example, less than or equal to about 0.05, for example less than or equal to about 0.01.

It is possible to give precedence to spectral sub-ranges in which the reflectance of the comparison sample 4 and the corresponding skin may be substantially closer, for example, in which $\Delta$ is much smaller. For example, particular preference can be optionally given to the spectral range from about 600 nm to about 750 nm, corresponding to red and its various shades. By way of example, $\Delta$ can be less than or equal to about 0.01 in this spectral range.

To obtain a desired reflectance spectrum for each comparison sample 4, it is possible to use known software that enables a composition of pigments to be determined that corresponds to a given reflectance spectrum. For example, it is possible to use Datamatch software from Datacolor International.

The color of the comparison samples 4 can be substantially uniform. Alternatively, the comparison samples 4 can be made to each present a color that is non-uniform. For example, the comparison samples may have local variations in hue and/or in lightness.

In cases of color non-uniformity, the spectral reflectance of a comparison sample 4 will correspond to a mean value, for example, for an area having a diameter of 1 centimeter (cm).

Patterns can be made on the comparison samples 4 so as to imitate skin texture, for example. Each comparison sample 4 may have areas of differing hues and/or lightnesses. This may be obtained by printing patterns of a color that differs from that of the color of the background, which may be a sepia color.

It also may be possible to imitate the appearance of the skin by using a medium (e.g., support) that presents relief.

As an example, a medium that has been embossed so as to imitate skin grain may be used. Embossing can be performed by calendering, for example, either before or after the color coating has been deposited.

Figure 6:
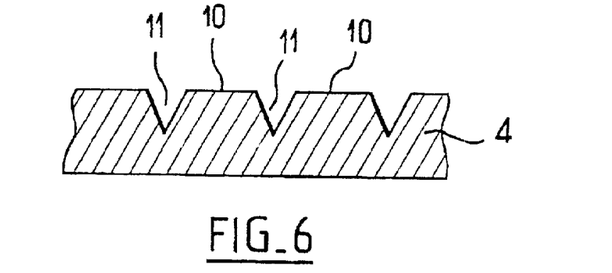
FIG. 6 is a partial cross-sectional view of an exemplary embodiment of comparison sample comprising reliefs.

To imitate skin appearance better, and in particular to imitate its locally more or less shiny character, it may be desirable to confer non-uniform brightness on the comparison samples 4. There are various ways in which non-uniform brightness can be obtained. In particular, it is possible to make plateaus 10 or recesses 11, as shown in FIG. 6.

Areas of color coating that match the shape of the recesses 11 then may appear to be less shiny than those covering the plateaus 10. Also, it is possible to apply gloss varnish to the plateaus 10, but not to the recesses 11.

It is also possible to imitate the appearance of the skin by optionally using a medium that represents relief, for example, a medium that has been embossed so as to substantially imitate skin grain. Embossing may be performed by calendering, for example, either before or after the color coating has been deposited.

Figure 7:
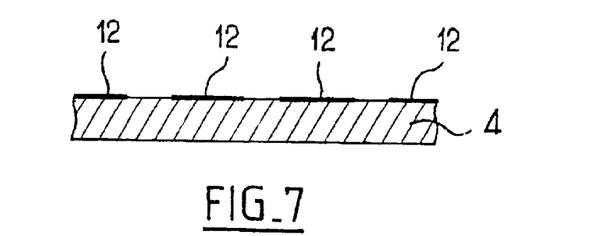
FIG. 7 is a partial cross-sectional view of an exemplary embodiment of comparison sample comprising gloss varnish.
Figure 12:
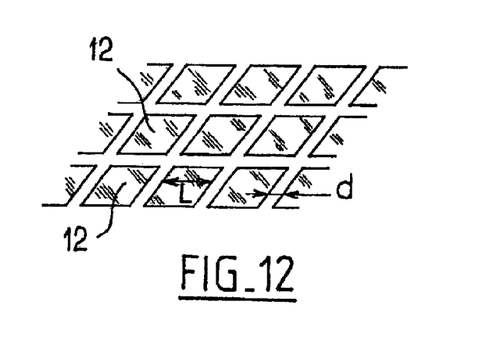
FIG. 12 is a plane view of an exemplary embodiment of coating to obtain regions of differing brightness.

It also may be possible to obtain non-uniform brightness by applying a gloss varnish 12 onto a plane medium, as shown in FIGS. 7 and 12. In this case, the varnish covers only a portion of the comparison sample, for example, the varnish may cover square shapes having side dimensions of approximately L=300 μm. These squares may be spaced apart from one another by distances of approximately d=100 μm.

Figure 8:
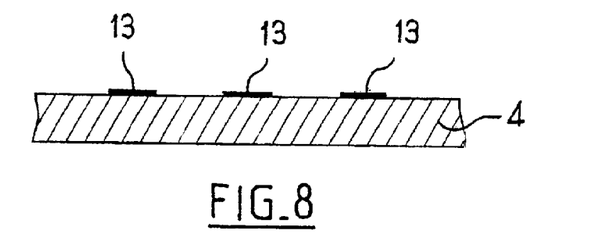
FIG. 8 is a partial cross-sectional view of yet another exemplary embodiment of a comparison sample comprising mat varnish.

In a variant, as shown in FIG. 8, it is possible to apply a mat varnish 13, for example, in the form of areas that are about 100 μm wide, and that are spaced apart from each other by a distance of about 300 μm.

Figure 9:
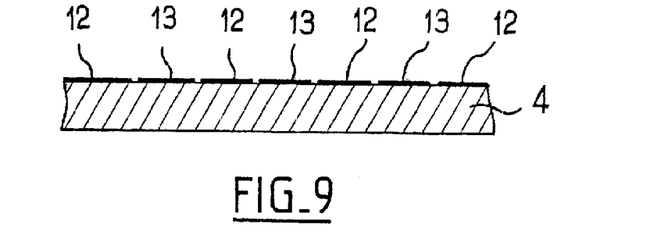
FIG. 9 is a partial cross-sectional view of another exemplary embodiment of a comparison sample comprising mat varnish and gloss varnish.

It also is possible to juxtapose or superpose a gloss varnish and a mat varnish. As shown in FIG. 9, the regions 12 of gloss varnish may be about 300 μm wide and the regions 13 of mat varnish may be about 100 μm.

A user of the chart or system may determine not only the color of the skin, but also the brightness that corresponds thereto, or other appearance characteristics other than color, such as relief or distribution of brightness or of color, for example.

The system can be used in numerous situations, in particular in the field of cosmetics. First, the system is useful for performing statistical studies in a population, for example, to extract typological characteristics of certain skin types.

The system also may enable a person to determine her skin color and brightness, for example. This may subsequently facilitate the purchase of cosmetics, especially foundation makeup, since the person may then select makeup that has been given the same identifier as that provided on the comparison sample substantially corresponding to the person's skin color and brightness. This may help to ensure the person has chosen the make-up having an appropriate color and brightness.

The system can also be useful when a person is seeking to apply a product that does not correspond exactly to that person's own skin color, but that presents differing lightness and/or hue, corresponding to a given comparison sample. Under such circumstances, and from the relative appearance characteristics of this comparison sample and the comparison sample corresponding to the skin appearance of the user, the user can determine how a color of interest is situated in terms of brightness and hue relative to the user's own skin.

The chart or system according to an exemplary embodiment of the invention may also be useful for determining variation in the color and/or brightness of the skin, following treatment by a product, such as a skin coloring (e.g., self-tanning) product, for example, or merely following exposure to the sun or to an artificial source of ultraviolet radiation. The chart or system may make it possible to determine whether a desired degree of suntan has been reached for a given person. If it has, then that person may know that further exposure is not necessary, and may avoid excessive exposure or may adopt special protection against the sun.

As an example, before exposing the skin, the user may match his or her current skin color to a comparison sample. After exposure, the person may again match his or her skin to a comparison sample to determine whether the skin has become darker in color. Also, the person may pick a comparison sample having a desired or recommended color. The person may expose his or her skin until its color becomes substantially similar to the selected sample.

The system further may be used to determine the effect of a cosmetic or care product on the color of the skin, such as, for example, a self-tanning lotion, a foundation or other make-up product. Under such circumstances, the user can determine the effectiveness of the treatment by making a comparison with a comparison sample used as a reference and corresponding to the color and appearance characteristic other than color of the skin before treatment begins.

The chart can be made available in physical form as shown in FIGS. 1 to 3. However, it would not go beyond the ambit of the present invention for the comparison samples to be supplied to the user in a non-physical form, such as in the form of a computer data file containing the information required to enable comparison samples to be printed or displayed on an appropriate medium, such as a monitor, for example.

Figure 10:
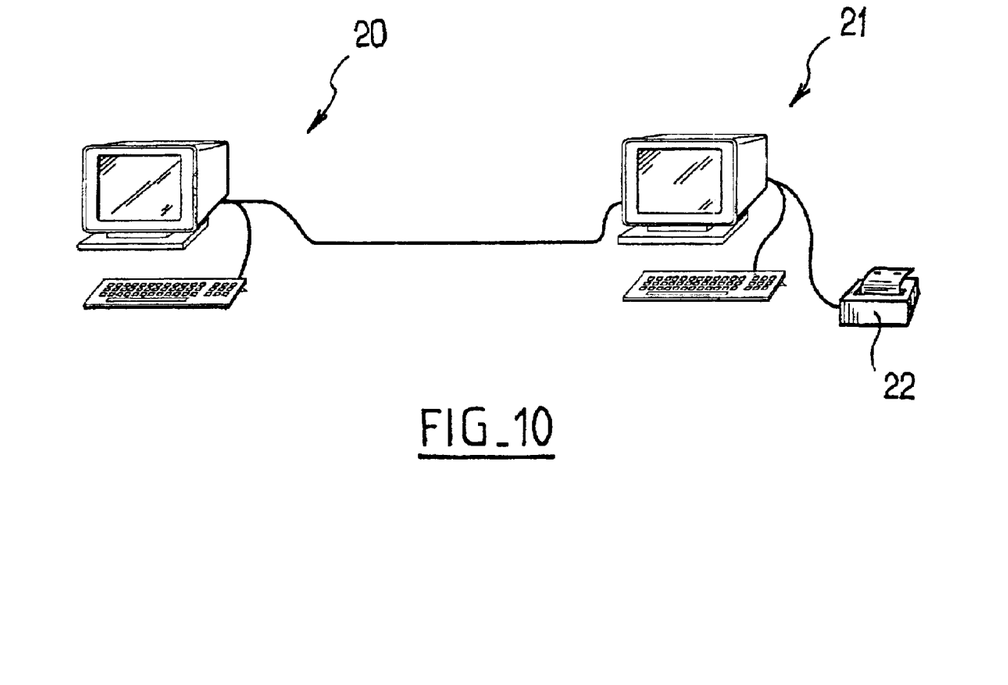
FIG. 10 is a schematic representation of an exemplary embodiment of a network system for displaying or printing comparison samples.

For example, FIG. 10 depicts a computer data file being transferred from a first computer 20 to a second computer 21, the file containing information relevant for printing various comparison samples on a suitable printer 22. For example, the first computer may be transmitting an image. Data may be transmitted between the computers 20 and 21 by means of a computer network, for example, the Internet, an intranet, or a local area network.

As discussed above, transmitting an image may involve transmission of the image through one or more networks and/or storage mediums. Networks may include public networks such as the Internet, telephony networks, courier networks (e.g. postal service, United Parcel Service, Federal Express, etc.), private networks, virtual private networks, local area networks, metropolitan area networks, wide area networks, ad hoc networks, or any other mechanism for permitting communication between remote sites, regardless of whether the connection is wired or wireless. In a broader sense, an image may be transmitted physically such as in hard copy form, via mail delivery, or other courier delivery. Storage mediums may include magnetic storage devices, such as floppy disks and hard drives; optical storage devices, such as compact discs and digital video discs; organic storage devices; random access memory; printed media; or any other medium for storing information.

Naturally, the invention is not limited to the embodiments described above. For example, it may be possible to provide comparison samples that substantially simulate the color and an appearance characteristic other than color, such as brightness, of the skin, including the lips, a fingernail, a toenail, or hair of predetermined type. The appearance characteristic other than color may include relief, non-uniformity of color, or non-uniformity of relief, and/or brightness, for example. When the appearance characteristic other than color includes relief, the comparison samples 4 may represent a plurality of types of relief, for example, for the purpose of representing different kinds of skin grain. Such comparison samples may be useful for determining the action of a product that may be intended to have an influence on the grain of the skin, for example, a product having a peeling action.

When the appearance characteristic other than color is non-uniformity of relief, the comparison samples 4 may represent relief that may vary in a plurality of degrees from a substantially uniform relief to relief that may be highly irregular, such as occurs during aging, so as to represent the manner in which the relief of the skin changes, for example.

When the appearance characteristic other than color is non-uniformity of color, at least two comparison samples may represent marks that are present in different numbers from one comparison sample to the other so as to substantially represent the manner in which marks may appear on the skin during aging, for example, because of the influence of the sun's rays.

Furthermore, sizes of various structural parts and materials used to make the above mentioned devices are illustrative and exemplary only, and one of ordinary skill in the art would recognize that these sizes and materials can be changed as necessary to produce differing effects or desired characteristics of the matching chart, the system, or the comparison samples. For example, the groupings of the comparison samples into sets can be accomplished in numerous ways and the ways discussed herein are merely exemplary. Indeed, a single comparison sample may be provided. Further, a comparison sample may be supplied individually on a product that corresponds in some way to the comparison sample.

It will be apparent to those skilled in the art that various modifications and variations can be made to the structure and methodology. Thus, it should be understood that the invention is not limited to the examples and embodiments discussed in the specification. Rather, the present invention is intended to cover modifications and variations.

What is claimed is:

1. A matching chart comprising:
   at least one comparison sample configured to simulate the appearance of a keratinous element,
   wherein the at least one comparison sample is configured to simulate a color and at least one appearance characteristic other than color of the keratinous element.

2. The matching chart of claim 1, further comprising a plurality of comparison samples, wherein each comparison sample is configured to simulate a color and at least one appearance characteristic other than color of the keratinous element.

3. The matching chart of claim 1, wherein the at least one appearance characteristic other than color comprises brightness.

4. The matching chart of claim 1, wherein the at least one appearance characteristic other than color comprises relief.

5. The matching chart of claim 1, wherein the at least one appearance characteristic other than color comprises color non-uniformity.

6. The matching chart of claim 1, wherein the at least one appearance characteristic other than color comprises non-uniformity of relief.

7. The matching chart of claim 1, wherein the at least one comparison sample is configured to have a non-uniform brightness.

8. The matching chart of claim 7, wherein the at least one comparison sample comprises at least one relatively shiny region, the at least one relatively shiny region comprising a gloss varnish.

9. The matching chart of claim 8, wherein a width of the at least one relatively shiny region is approximately 300 micrometers.

10. The matching chart of claim 7, wherein the at least one comparison sample comprises a relatively dull region, the relatively dull region comprising a mat varnish.

11. The matching chart of claim 10, wherein a width of the at least one relatively dull region is approximately 100 micrometers.

12. The matching chart of claim 1, wherein the at least one comparison sample comprises a relief pattern, the relief pattern being configured to provide a non-uniform brightness.

13. The matching chart of claim 12, wherein the relief pattern comprises at least one recess and at least one plateau.

14. The matching chart of claim 13, wherein the at least one plateau is coated with a gloss varnish.

15. The matching chart of claim 14, wherein the at least one recess is not coated with a gloss varnish.

16. The matching chart of claim 1, wherein the at least one comparison sample is configured to have a substantially uniform brightness.

17. The matching chart of claim 1, wherein each comparison sample comprises a support having a substantially rectangular shape.

18. The matching chart of claim 17, wherein the support has a width of approximately 60 millimeters and a length of approximately 100 millimeters.

19. The matching chart of claim 17, wherein the color and the at least one appearance characteristic other than color are provided on at least a surface portion of the support.

20. The matching chart of claim 1, wherein the at least one comparison sample defines a hole configured to permit observation of the keratinous element through the hole.

21. The matching chart of claim 20, wherein the hole is located at about one third of the length of the comparison sample.

22. The matching chart of claim 20, wherein the hole has a dimension of approximately 20 millimeters.

23. The matching chart of claim 22, wherein the hole is circular and the dimension is a diameter.

24. The matching chart of claim 1, wherein the at least one comparison sample includes an identifier associated with the color and the at least one appearance characteristic other than color of the sample.

25. The matching chart of claim 24, wherein the identifier is an alphanumeric code.

26. The matching chart of claim 1, wherein the at least one comparison sample is configured to simulate the appearance of a keratinous element chosen from hair, skin, a fingernail, and a toenail.

27. The matching chart of claim 1, wherein the at least one comparison sample is configured to be displayed on a package of a product intended for application to a keratinous element.

28. A system comprising:
   a plurality of comparison samples, each comparison sample being configured to simulate an appearance of a keratinous element,
   wherein each comparison sample is configured to simulate a color and at least one appearance characteristic other than color of the keratinous element.

29. The system of claim 28, wherein the at least one appearance characteristic other than color comprises brightness.

30. The system of claim 29, wherein at least two comparison samples are configured to have differing brightnesses.

31. The system of claim 28, wherein the at least one appearance characteristic other than color comprises relief.

32. The system of claim 31, wherein at least two comparison samples are configured to have differing degrees of relief.

33. The system of claim 28, wherein the at least one appearance characteristic other than color comprises color non-uniformity.

34. The system of claim 33, wherein at least two comparison samples are configured to have color non-uniformly distributed within each sample in a differing manner from each other.

35. The system of claim 34, wherein the at least two comparison samples comprise a background color and marks distributed on the background color, the marks being of a color that differs from the background color,
   wherein one of the at least two comparison samples comprises at least one of a differing number of marks, a differing distribution of marks, and a differing size of marks from the other of the at least two comparison samples.

36. The system of claim 28, wherein the at least one appearance characteristic other than color comprises non-uniformity of relief.

37. The system of claim 36, wherein at least two comparison samples have differing distributions of relief.

38. The system of claim 28, further comprising at least three comparison samples, each comparison sample being configured to simulate at least one of a color and an appearance characteristic other than color that differs from the other comparison samples.

39. The system of claim 38, wherein the at least three comparison samples comprise four comparison samples.

40. The system of claim 38, wherein the at least three comparison samples comprise five comparison samples.

41. The system of claim 28, wherein each of the comparison samples is configured to have a non-uniform brightness.

42. The system of claim 41, wherein each of the comparison samples comprises at least one relatively shiny region, the at least one relatively shiny region comprising a gloss varnish.

43. The system of claim 42, wherein a width of the at least one relatively shiny region is approximately 300 micrometers.

44. The system of claim 41, wherein each of the comparison samples comprises at least one relatively dull region, the at least one relatively dull region comprising a mat varnish.

45. The system of claim 44, wherein a width of the at least one relatively dull region is approximately 100 micrometers.

46. The system of claim 28, wherein the comparison samples comprise a relief pattern, the relief pattern being configured to provide a non-uniform brightness.

47. The system of claim 46, wherein the relief pattern comprises at least one recess and at least one plateau.

48. The system of claim 47, wherein the at least one plateau is coated with a gloss varnish.

49. The system of claim 48, wherein the at least one recess is not coated with a gloss varnish.

50. The system of claim 28, wherein each of the comparison samples is configured to have a substantially uniform brightness.

51. The system of claim 28, wherein each comparison sample comprises a support having a substantially rectangular shape.

52. The system of claim 51, wherein the support has a width of approximately 60 millimeters and a length of approximately 100 millimeters.

53. The system of claim 51, wherein the color and the at least one appearance characteristic other than color are provided on at least a surface portion of the support.

54. The system of claim 28, wherein each comparison sample defines a hole configured to permit observation of the keratinous element through the hole.

55. The system of claim 54, wherein the hole is located at about one third of the length of the comparison sample.

56. The system of claim 54, wherein the hole has a dimension of approximately 20 millimeters.

57. The system of claim 56, wherein the hole is circular and the dimension is a diameter.

58. The system of claim 28, wherein each comparison sample comprises an identifier associated with the color and the at least one appearance characteristic other than color of the sample.

59. The system of claim 58, wherein the identifier is an alphanumeric code.

60. The system of claim 28, wherein the comparison samples are configured to simulate the appearance of a keratinous element chosen from hair, skin, a fingernail, and a toenail.

61. The system of claim 28, wherein each of the comparison samples is configured to be displayed respectively on a package of a product intended for application to a keratinous element.

62. The system of claim 28, wherein the comparison samples are configured to be displayed via an electronic image.

63. The system of claim 28, further comprising at least one set of comparison samples, wherein the at least one set comprises at least some of the plurality of comparison samples having at least one of substantially the same color and substantially the same at least one appearance characteristic other than color.

64. A method of manufacturing a product intended for application to a keratinous element, the method comprising:
   providing the system of claim 28;
   selecting at least one of the plurality of comparison samples; and
   making a product intended for application to a keratinous element according to the color and the appearance characteristic other than color of the at least one selected comparison sample.

65. The method of claim 64, wherein the selecting of the at least one comparison sample comprises determining which of the plurality of comparison samples substantially corresponds to a color and an appearance characteristic other than color of the keratinous element to which the product is intended to be applied.

66. The method of claim 65, wherein the keratinous element is chosen from hair, skin, a fingernail, and a toenail.

67. The method of claim 64, wherein the selecting of the at least one comparison sample comprises determining which of the comparison samples substantially corresponds to a color and an appearance characteristic other than color desired by a user of the product.

68. The method of claim 64, wherein the product is chosen from at least one of a cosmetic product and a care product.

69. The method of claim 68, wherein the product is chosen from a foundation makeup product, a concealer product, a lip makeup product, a hair coloring product, a hair care product, a nail varnish, a blush, an eyeshadow, a skin coloring product, and a skin care product.

70. The method of claim 64, wherein the at feast one appearance characteristic other than color comprises brightness.

71. The method of claim 70, wherein at least two comparison samples are configured to have differing brightnesses.

72. The method of claim 64, wherein the at least one appearance characteristic other than color comprises relief.

73. The method of claim 72, wherein at least two comparison samples are configured to have differing degrees of relief.

74. The method of claim 64, wherein the at least one appearance characteristic other than color comprises color non-uniformity.

75. The method of claim 74, wherein at least two comparison samples are configured to have color non-uniformly distributed within each sample in a differing manner from each other.

76. The method of claim 75, wherein the at least two comparison samples comprise a background color and marks distributed on the background color, the marks being of a color that differs from the background color,
wherein one of the at least two comparison samples comprises at least one of a differing number of marks, a differing distribution of marks, and a differing size of marks from the other of the at least two comparison samples.

77. The method of claim 64, wherein the at least one appearance characteristic other than color comprises non-uniformity of relief.

78. The method of claim 77, wherein at least two comparison samples have differing distributions of relief.

79. The method of claim 64, further comprising at least three comparison samples, each comparison sample being configured to simulate at least one of a color and an appearance characteristic other than color that differs from the other comparison samples.

80. The method of claim 64, wherein each of the comparison samples is configured to have a non-uniform brightness.

81. The method of claim 80, wherein each of the comparison samples comprises at least one relatively shiny region, the at least one relatively shiny region comprising a gloss varnish.

82. The method of claim 80, wherein each of the comparison samples comprises at least one relatively dull region, the at least one relatively dull region comprising a mat varnish.

83. The method of claim 64, wherein each of the comparison samples comprises a relief pattern, the relief pattern being configured to provide a non-uniform brightness.

84. The method of claim 83, wherein the relief pattern comprises at least one recess and at least one plateau.

85. The method of claim 84, wherein the at least one plateau is coated with a gloss varnish.

86. The method of claim 85, wherein the at least one recess is not coated with a gloss varnish.

87. The method of claim 64, wherein each of the comparison samples is configured to have a substantially uniform brightness.

88. The method of claim 64, wherein the providing of the system comprises providing the plurality of comparison samples as a set.

89. The method of claim 65, wherein the determining which comparison sample substantially corresponds to the color and the at least one appearance characteristic other than color of the keratinous element comprises placing the keratinous element adjacent to at least a portion of the comparison sample so as to permit comparison of the keratinous element with the comparison sample.

90. The method of claim 64, wherein each comparison sample comprises an identifier associated with at least one of the color and the at least one appearance characteristic other than color of the sample, and wherein the making of the product further comprises making the product based on the identifier of the selected comparison sample.

91. The method of claim 90, wherein the identifier is an alphanumeric code.

92. A method of monitoring treatment of a keratinous element with a product, the method comprising:
providing the system of claim 28;
selecting a comparison sample that substantially corresponds to a color and at least one appearance characteristic other than color of the keratinous element;
applying a product to the keratinous element; and
determining whether at least one of the color and the at least one appearance characteristic other than color of the keratinous element to which the product has been applied has changed after applying the product by comparing the keratinous element with the comparison samples of the system.

93. The method of claim 92, wherein the at least one appearance characteristic other than color comprises brightness.

94. The method of claim 93, wherein the product affects the brightness of the keratinous element.

95. The method of claim 93, wherein at least two comparison samples are configured to have differing brightnesses.

96. The method of claim 92, further comprising selecting from a plurality of differing products the product to be applied to the keratinous element, wherein the selecting of the product is based upon the selected comparison sample.

97. The method of claim 96, wherein each of the comparison samples comprises an identifier associated with the color and the at least one appearance characteristic other than color of the sample, and wherein each of the plurality of differing products comprises an identifier matching one of the identifiers of the comparison samples, and wherein the selecting of the product comprises selecting the product comprising the identifier that matches the identifier of the selected comparison sample.

98. The method of claim 92, wherein the keratinous element is chosen from skin, hair, a fingernail, and a toenail.

99. The method of claim 92, wherein the product is chosen from a cosmetic product and a care product.

100. The method of claim 99, wherein the product is chosen from a foundation makeup product, a concealer makeup product, a lip makeup product, a hair coloring product, a hair care product, a nail varnish, a blush, an eyeshadow, a skin coloring product, and a skin care product.

101. The method of claim 92, wherein the product affects the relief of the keratinous element.

102. The method of claim 92, wherein the product affects the color of keratinous element.

103. The method of claim 92, wherein the at least one appearance characteristic other than color comprises relief.

104. The method of claim 92, wherein the at least one appearance characteristic other than color comprises color non-uniformity.

105. The method of claim 104, wherein at least two comparison samples comprise a background color and marks distributed on the background color, the marks being of a color that differs from the background color,
wherein one of the at least two comparison samples comprises at least one of a differing number of marks, a differing distribution of marks, and a differing size of marks from the other of the at least two comparison samples.

106. The method of claim 92, wherein the at least one appearance characteristic other than color comprises non-uniformity of relief.

107. The method of claim 92, further comprising at least three comparison samples, each comparison sample being configured to simulate at least one of a color and an appearance characteristic other than color that differs from the other comparison samples.

108. The method of claim 92, wherein each of the comparison samples is configured to have a non-uniform brightness.

109. The method of claim 108, wherein each of the comparison samples comprises at least one relatively shiny region, the at least one relatively shiny region comprising a gloss varnish.

110. The method of claim 108, wherein each of the comparison samples comprises at least one relatively dull region, the at least one relatively dull region comprising a mat varnish.

111. The method of claim 92, wherein each of the comparison samples comprises a relief pattern, the relief pattern being configured to provide a non-uniform brightness.

112. The method of claim 111, wherein the relief pattern comprises at least one recess and at least one plateau.

113. The method of claim 92, wherein each of the comparison samples is configured to have a substantially uniform brightness.

114. The method of claim 92, wherein providing the system comprises providing a plurality of comparison samples as a set.

115. The method of claim 92, wherein the comparing of the keratinous element with the comparison samples comprises placing the keratinous element adjacent to at least a portion of the comparison sample.

116. A method of selecting a product for application to a keratinous element, the method comprising:
providing the system of claim 28;
selecting a comparison sample of the system having a color and at least one appearance characteristic other than color that substantially corresponds to the keratinous element to which product is to be applied; and
selecting a product from a plurality of differing products for application to the keratinous element based on the selected comparison sample.

117. The method of claim 116, wherein each of the comparison samples comprises an identifier associated with the color and the at least one appearance characteristic other than color of the sample, and wherein the selecting of the product is based on the identifier of the selected comparison sample.

118. The method of claim 117, wherein each of the plurality of products comprises an identifier that matches one of the identifiers of the comparison samples, and wherein the selecting of the product comprises selecting the product comprising an identifier that matches the identifier of the selected comparison sample.

119. The method of claim 116, wherein the at least one appearance characteristic other than color comprises brightness.

120. The method of claim 116, wherein the product is chosen from a cosmetic product and a care product.

121. The method of claim 120, wherein the product is chosen from a foundation makeup product, a concealer product, a lip makeup product, a hair coloring product, a hair care product, a nail varnish, a blush, an eyeshadow, a skin coloring product, and a skin care product.

122. The method of claim 116, wherein the keratinous element is chosen from hair, skin, a fingernail, and a toenail.

123. The method of claim 117, wherein the identifier comprises an alphanumeric code.

124. The method of claim 116, wherein a color and a brightness differs for each of the plurality of products.

125. The method of claim 116, wherein the product affects the relief of the keratinous element.

126. The method of claim 116, wherein the product affects the color of the keratinous element.

127. The method of claim 116, wherein the at least one appearance characteristic other than color comprises relief.

128. The method of claim 116, wherein the at least one appearance characteristic other than color comprises color non-uniformity.

129. The method of claim 128, wherein at least two comparison samples comprise a background color and marks distributed on the background color, the marks being of a color that differs from the background color,
wherein one of the at least two comparison samples comprises at least one of a differing number of marks, a differing distribution of marks, and a differing size of marks from the other of the at least two comparison samples.

130. The method of claim 116, wherein the at least one appearance characteristic other than color comprises non-uniformity of relief.

131. The method of claim 116, further comprising at least three comparison samples, each comparison sample being configured to simulate at least one of a color and an appearance characteristic other than color that differs from the other comparison samples.

132. The method of claim 116, wherein each of the comparison samples is configured to have a non-uniform brightness.

133. The method of claim 132, wherein each of the comparison samples comprises at least one relatively shiny region, the at least one relatively shiny region comprising a gloss varnish.

134. The method of claim 133, wherein each of the comparison samples comprises at least one relatively dull region, the at least one relatively dull region comprising a mat varnish.

135. The method of claim 116, wherein each of the comparison samples comprises a relief pattern, the relief pattern being configured to provide a non-uniform brightness.

136. The method of claim 135, wherein the relief pattern comprises at least one recess and at least one plateau.

137. The method of claim 116, wherein each of the comparison samples is configured to have a substantially uniform brightness.

138. The method of claim 116, wherein providing the system comprises providing a plurality of comparison samples as a set.

139. The method of claim 116, further comprising comparing the keratinous element to each of the comparison samples to determine which comparison sample has a color and an appearance characteristic other than color that substantially corresponds to the keratinous element.

140. The method of claim 139, wherein the comparing comprises placing the keratinous element adjacent to at least a portion of the comparison sample.

141. The method of claim 116, further comprising providing each of the plurality of comparison samples on a respective package associated with each of the plurality of differing products.

142. A method of treating a keratinous element, the method comprising:

providing the system of claim 28;

selecting a comparison sample from the system that corresponds to a desired color and at least one appearance characteristic other than color for the keratinous element;

treating the keratinous element based on the selected comparison sample.

143. The method of claim 142, wherein the treating comprises applying a product to the keratinous element.

144. The method of claim 142, further comprising selecting a product for treating the keratinous element from a plurality of differing products, wherein the selecting is based on the selected comparison sample.

145. The method of claim 144, wherein each comparison sample comprises an identifier associated with the color and at least one appearance characteristic other than color of the sample, and wherein the selecting of the product is based on the identifier of the selected comparison sample.

146. The method of claim 145, wherein each of the plurality of products comprises an identifier that matches one of the identifiers of the comparison samples, and wherein the selecting of the product comprises selecting the product comprising an identifier that matches the identifier of the selected comparison sample.

147. The method of claim 142, wherein the product is chosen from a cosmetic product and a care product.

148. The method of claim 147, wherein the product is chosen from a foundation makeup product, a concealer makeup product, a lip makeup product, a hair coloring product, a hair care product, a nail varnish, a blush, an eyeshadow, a skin coloring product, and a skin care product.

149. The method of claim 142, wherein the keratinous element is chosen from hair, skin, a fingernail, and a toenail.

150. The method of claim 142, wherein the at least one appearance characteristic other than color comprises brightness.

151. The method of claim 142, wherein the at least one appearance characteristic other than color comprises relief.

152. The method of claim 142, wherein the at least one appearance characteristic other than color comprises color non-uniformity.

153. The method of claim 142, wherein the providing the system comprises providing the plurality of comparison samples as a set.

154. The method of claim 144, further comprising providing each of the plurality of comparison samples on a respective package associated with each of the plurality of differing products.

155. A method of enabling an analysis of a keratinous element, the method comprising:

transmitting at least one image simulating an appearance of a keratinous element, wherein the image is configured to simulate a color and at least one appearance characteristic other than color of the keratinous element; and comparing the keratinous element with the at least one image to determine if the at least one image substantially corresponds to the color and the at least one appearance characteristic other than color of the keratinous element.

156. The method of claim 155, wherein the transmitting of the image comprises transmitting the image via a network.

157. A method of enabling an analysis of a keratinous element, the method comprising:

transmitting at least one image simulating an appearance of a keratinous element, wherein the image is configured to simulate a color and at least one appearance characteristic other than color of the keratinous element; and receiving information relating to a comparison between at least one keratinous element and the at least one image.

* * * * *

UNITED STATES PATENT AND TRADEMARK OFFICE
CERTIFICATE OF CORRECTION

PATENT NO. : 6,724,480 B2
DATED : April 20, 2004
INVENTOR(S) : Jean de Rigal et al.

It is certified that error appears in the above-identified patent and that said Letters Patent is hereby corrected as shown below:

Column 16,
Line 55, "of Keratinous" should read -- of the keratinous --.

Signed and Sealed this

Twelfth Day of April, 2005

JON W. DUDAS
*Director of the United States Patent and Trademark Office*